US00PP23548P2

(12) United States Plant Patent
Kordes

(10) Patent No.: US PP23,548 P2
(45) Date of Patent: Apr. 23, 2013

(54) SHRUB ROSE PLANT NAMED 'KORSIXKONO'

(50) Latin Name: *Rosa hybrida*
Varietal Denomination: KORsixkono

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/135,653

(22) Filed: Jul. 11, 2011

(51) Int. Cl.
*A01H 5/00* (2006.01)

(52) U.S. Cl. ..... Plt./108

(58) Field of Classification Search ..... Plt./108
See application file for complete search history.

*Primary Examiner* — Kent L Bell

(57) ABSTRACT

A new and distinct variety of rose with long lasting, novel red flowers, and attractive foliage with excellent disease resistance. It exhibits moderately vigorous growth with upright, bushy habit and abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORsixkono'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2001. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORsixkono'.

SUMMARY OF THE INVENTION

The new rose plant may be distinguished from its seed parent, an 'un-named seedling', by the following combination of characteristics:

1. The disease resistance of 'KORsixkono' has excellent disease resistance while the disease resistance of the seed parent is good.
2. The flower size of 'KORsixkono' is medium while the flower size of the seed parent is small.

The new rose plant may be distinguished from its pollen parent, an 'un-named seedling' by the following combination of characteristics:

1. The flower color of 'KORsixkono' is red while the flower color of the pollen parent is crimson.
2. The foliage of 'KORsixkono' is glossy while the foliage of the pollen parent is matte.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORsixkono' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORsixkono' was selected in May, 2002 from the seedling beds to be asexually propagated for further evaluation. The first asexual propagation of 'KORsixkono' was done by budding to seedling understocks in July, 2002 at the inventor's nursery in Offenseth-Sparrieshoop, Germany.

This initial and other subsequent propagations conducted in controlled environments demonstrate that 'KORsixkono' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORsixkono'.

DETAILED BOTANICAL DESCRIPTION

The following is a description of 'KORsixkono', as observed growing in June, 2011 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORcasima', a rose variety from the same inventor described and illustrated in U.S. Plant Pat. No. 20,732 and issued on Feb. 9, 2011 are compared to 'KORsixkono' in Chart 1.

CHART 1

| Characteristic | 'KORsixkono' | 'KORcasima' |
|---|---|---|
| Color, upper petal surface at ¼ open: | Red Group 46A. | Red Group 53A. |
| Petal count: | Approximately 16-18. | Approximately 70-80. |
| Petaloid count: | Average range of 0-4. | Average range of 2-5. |

Parents:

*Seed parent.*—An 'un-named seedling'.

*Pollen parent.*—An 'un-named seedling'.

Classification:

*Botanical classification.—Rosa hybrida* 'KORsixkono'.

*Commercial classification.*—Shrub rose.

FLOWER AND FLOWER BUD

Blooming habit: Continuous.

Flower bud:

*Size.*—Upon opening, 20 mm in length from base of receptacle to end of bud and 10 mm diameter at its widest point.

*Bud form.*—Short. Pointed ovoid.

*Bud color.*—As sepals first unfold, bud color is Red Group 46A. When ¼ open, the upper surface of petals is Red Group 46A, and the lower surface is between Red-Purple Group N66 & Red Group 46B.

*Sepals.*—Color: Upper surface Yellow-Green Group 146B. Lower surface Green Group 146A, with intonations of Greyed-Purple Group 184B. Size: Average 20-25 mm (l)×7-8 mm (w). Base: Flat at union with receptacle. Shape: Triangular. Sepals generally subulate. Sepal apex is apiculate. Strong foliaceous appendages on two of the five sepals. Quantity: Five. Surface texture: Upper side: Smooth with heavy pubescence. Lower surface: Rough with moderate pubescence. Margins: Pubescent with limited numbers of stipitate glands.

Receptacle:

*Surface.*—Smooth with occasional fine hairs.

*Color.*—Yellow-Green Group 146B, with intonations of Greyed-Purple Group 183D.

*Shape.*—Urn-shaped.

*Size.*—8 mm (h)×7 mm (w).

Peduncle:

*Surface.*—With stipitate glands.

*Length.*—30 to 50 mm average length.

*Diameter.*—1-2 mm average diameter.

*Color.*—Yellow-Green Group 146C.

*Strength.*—Somewhat strong.

*Borne.*—Multiple flower buds per stem, generally 3 to 4.

Flower bloom:

*Fragrance.*—None.

*Duration.*—On the plant 3-4 days. As a cut flower, 2-4 days. Senesced petals drop away cleanly.

*Size.*—Medium. When open, the average flower diameter is 60-75 mm and the average flower height is 20-25 mm.

*Form.*—Shape of flower when viewed from the side: Upon opening, upper part: Flat. Upon opening, lower part: Concave. Open flower, upper part: Convex. Open flower, lower part: Concave.

Color:

*Upon opening, petals.*—Outermost petals: Outer Side: Red Group 53C. Inner Side: Red Group 46B. Innermost petals: Outer Side: Red Group 53C. Inner Side: Red Group 46B.

*Upon opening, basal petal spots.*—Basal petal spot, outermost petals: Outer Side: Green-Yellow Group 1B and 1C. Inner Side: Green-Yellow Group 1C. Basal petal spot, innermost petals: Outer Side: Yellow-Green Group 1B. Inner Side: Green-Yellow Group 1A.

*After opening, petals.*—Outermost petals: Outer Side: Red Group 53C. Inner Side: Red Group 46B. Innermost petals: Outer Side: Red Group 53B. Inner Side: Red Group 46B.

*After opening, basal petal spots.*—Basal petal spot, outermost petals: Outer Side: Yellow Group 4D. Inner Side: Green-Yellow Group 1D. Basal petal spot, innermost petals: Outer Side: Yellow Group 4D. Inner Side: Green-Yellow Group 1D.

General tonality: On open flower Red Group 53B. No change in the general tonality at the end of the 3$^{rd}$ day. Afterwards, general tonality is Red Group 46B.

Petals:

*Petal count.*—Double. Average Range: Approximately 16 petals under normal conditions.

*Petal reflex.*—Petals reflex somewhat.

*Petal edge.*—Variable. Entire to slightly lobed.

*Petal shape.*—Obtuse. Apex shape is obtuse with slight indentation in center. Shape of base is deltoid.

*Petal size.*—35-40 mm (l)×25-30 mm (w).

*Thickness.*—Average.

*Petal arrangement.*—Not formal.

Petaloids: Usually a few present.

*Petaloid count.*—Average of 0-4 per flower.

*Petaloid Size:* 5 mm (l)×2 mm (w).

*Petaloid color.*—Color of inner side is Red Group 53B. Color of outer side is Red Group 53A and 53B.

*Petaloid texture.*—Fine.

*Margin.*—Indented.

*Petaloid shape.*—Irregular. Apex: Deltoid. Base: Linear.

Reproductive organs:

*Pistils.*—Approximately 15-18 present. Stigmas: Location: Slightly inferior in position to anthers. Color: Greyed-Yellow Group 160C. Styles: Length: 3 mm long. Color: Yellow Group 145B at base. Intonations of Greyed-Purple Group 184C below stigma.

*Stamens.*—Approximately 30-35 on average and regularly arranged around the styles. Anthers: Size: 1 mm average length. Pollen: Generally present. Color: Greyed-Orange Group 163B and 163C. Filaments: Color: Yellow-Green Group 154C. Length: 7-8 mm average length.

THE PLANT

Growth: Moderately vigorous.

Plant habit: Bushy to upright. When grown as a field grown plant, the average plant height is 90 cm and the average plant width is 50 cm.

Stems:

*Stem color*.—Young wood: Yellow-Green Group 144A. Older wood: Yellow-Green Group 146B.

*Stem surface*.—Young wood: Smooth. Older wood: Smooth.

Prickles: Present.

*Incidence*.—On average, 10 per each 10 cm of stem.

*Size*.—Average length: 5 mm.

*Color*.—Immature prickles: Greyed-Red Group 182C. Mature prickles: Greyed-Red Group 183D. Senescing to Brown Group 200C.

*Shape*.—Concave.

*Anthocyanin*.—Not observed.

Leaves and leaflets: Normally 7 leaflets on normal leaves in middle of the stem. The two basal leaflets of the leaf are significantly smaller than the others.

*Venation pattern*.—Pyramidal net pattern.

*Leaf size*.—10 mm (l)×80 mm (w).

*Abundance*.—Average.

*Texture*.—Thick. Upper side of leaflet: Semi-glossy and glabrous. Under side of leaflet: Matte.

*Color, mature foliage*.—Upper Leaf Surface: Green Group 137A. Lower Leaf Surface: Green Group 137C.

*Color, juvenile foliage*.—Upper Leaf Surface: Green Group 137A. Lower Leaf Surface: Yellow-Green Group 146A.

*Anthocyanin intonation*.—Present. Intonations of Greyed-Purple Group 184C on center vein and leaf margins.

Stipules:

*Size*.—Average 14 mm long. Main body of stipule 4 mm in width.

*Stipule color*.—Yellow-Green Group 146B.

*Anthocyanin*.—Greyed-Red Group 184C.

*Stipitate glands*.—Present along margins.

*Shape*.—Apex: Apiculate. Base: Flat.

Petiole:

*Length*.—Average 8-9 mm.

*Diameter*.—Average 1-2 mm.

*Petiole color*.—Yellow Group 146C.

*Texture*.—Upper side of petiole is rough, lower side pubescent.

*Margins*.—With limited stipitate glands and slight pubescence.

*Anthocyanin*.—Upper margins with intonations of Greyed-Red Group 182B and 182C.

*Prickles*.—Lacking.

Petiole rachis:

*Length*.—10-15 mm.

*Diameter*.—1-2 mm.

*Color*.—Yellow-Green Group 146D.

*Underneath*.—Glabrous.

*Margins*.—With stipitate glands.

*Anthocyanin*.—More prominent on upper side. Greyed-Purple Group 186D.

*Prickles*.—Lacking.

*Stipitate glands*.—Limited numbers of stipitate glands at point of leaf attachment.

Leaflets:

*Size*.—Average size of the terminal leaflet is 40 mm (l)×25 mm (w).

*Shape*.—Entire leaflet: Ovate. Base: Obtuse. Apex: Acute.

*Margins*.—Finely serrated.

*Surface*.—Upper: Moderately glossy. Lower: Matte.

*Texture*.—Leathery.

*Arrangement*.—Odd pinnate.

Hips/seed formation: None observed.

Winter hardiness: To date, the variety has been grown successfully in Zones 5-9.

Disease resistance: Excellent resistance to Powdery mildew (*Sphaerotheca pannosa*), rust (*Phragmidium disciflorum*), and blackspot (*Diplocarpon rosae*) diseases under normal growing conditions.

I claim:

1. A new and distinct variety of rose plant, as described and illustrated herein.

* * * * *

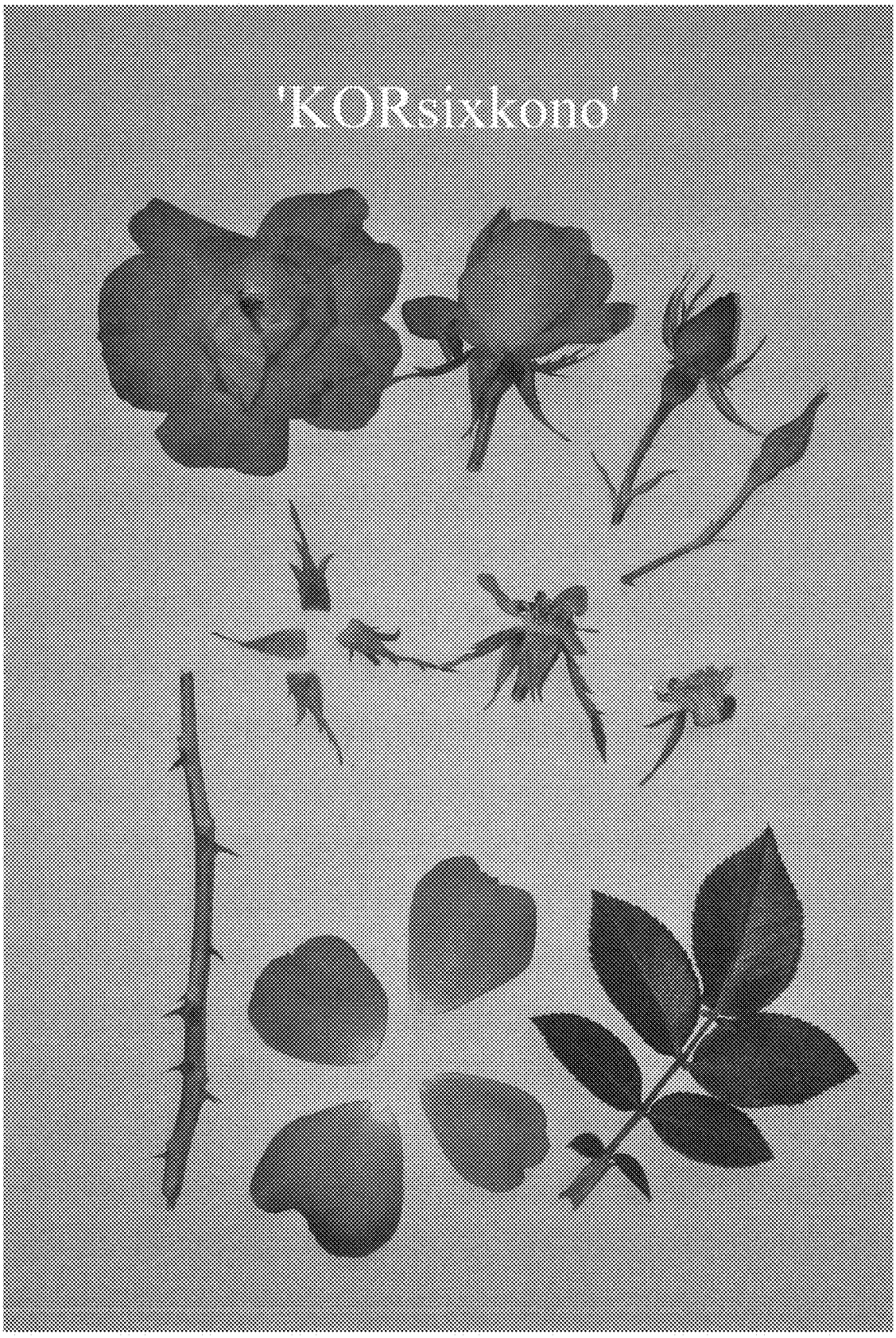
'KORsixkono'